(12) United States Patent
Destainville et al.

(10) Patent No.: US 12,121,275 B2
(45) Date of Patent: Oct. 22, 2024

(54) BONE ANCHORING SCREWS PROVIDED WITH A PLURALITY OF SOCKET TYPES

(71) Applicant: ABYS MEDICAL, La Rochelle (FR)

(72) Inventors: Arnaud Destainville, Saint-Xandre (FR); Olivier Richart, La Rochelle (FR)

(73) Assignee: ABYS MEDICAL, La Rochelle (FR)

( * ) Notice: Subject to any disclaimer, the term of this patent is extended or adjusted under 35 U.S.C. 154(b) by 395 days.

(21) Appl. No.: 17/595,904

(22) PCT Filed: May 15, 2020

(86) PCT No.: PCT/FR2020/050815
§ 371 (c)(1),
(2) Date: Nov. 29, 2021

(87) PCT Pub. No.: WO2020/240111
PCT Pub. Date: Dec. 3, 2020

(65) Prior Publication Data
US 2022/0313329 A1 Oct. 6, 2022

(30) Foreign Application Priority Data
May 28, 2019 (FR) ...................................... 1905657

(51) Int. Cl.
*A61B 17/86* (2006.01)
(52) U.S. Cl.
CPC ................................ *A61B 17/8615* (2013.01)
(58) Field of Classification Search
CPC ................................................. A61B 17/8615
See application file for complete search history.

(56) References Cited

U.S. PATENT DOCUMENTS

| | | |
|---|---|---|
| 9,044,843 B1 | 6/2015 | Mokhtee |
| 2003/0059276 A1* | 3/2003 | Chen ................ F16B 23/0092 411/403 |
| 2006/0266168 A1 | 11/2006 | Pacheco |
| 2009/0010734 A1 | 1/2009 | Lin |
| 2009/0220321 A1 | 9/2009 | Sakamura |
| 2014/0142639 A1 | 5/2014 | Vennard et al. |
| 2017/0238982 A1 | 8/2017 | Alicastro |
| 2018/0347612 A1 | 12/2018 | Falkenstein et al. |

FOREIGN PATENT DOCUMENTS

| | | |
|---|---|---|
| EP | 0172130 B1 | 4/1989 |
| EP | 2278175 | 2/2013 |
| WO | 2003/025403 | 3/2003 |

OTHER PUBLICATIONS

International Search Report for International Application No. PCT/FR2020/050815 dated Aug. 18, 2020, 3 pages.
International Written Opinion for International Application No. PCT/FR2020/050815 dated Aug. 18, 2020, 7 pages.

* cited by examiner

*Primary Examiner* — Olivia C Chang
(74) *Attorney, Agent, or Firm* — TraskBritt

(57) ABSTRACT

A bone anchoring screw comprises a head, a shaft and a threaded portion arranged successively along a common axis, the head having a recess comprising at least two stages arranged in succession along the common axis, the first stage having a diameter larger than the diameter of the second stage, in which one of the two stages comprises at least one socket of a first type and the other of the two stages comprises at least one socket of the first type and one other type.

18 Claims, 5 Drawing Sheets

BONE ANCHORING SCREWS PROVIDED WITH A PLURALITY OF SOCKET TYPES

CROSS-REFERENCE TO RELATED APPLICATIONS

This application is a national phase entry under 35 U.S.C. § 371 of International Patent Application PCT/FR2020/050815, filed May 15, 2020, designating the United States of America and published as International Patent Publication WO 2020/240111 A1 on Dec. 3, 2020, which claims the benefit under Article 8 of the Patent Cooperation Treaty to French Patent Application Serial No. FR1905657, filed May 28, 2019.

TECHNICAL FIELD

The present disclosure relates to a screw provided with a plurality of socket types, in particular, for use thereof in a medical context, in particular, in that of orthopedic, maxillofacial or dental surgery.

BACKGROUND

In the present description, the term "screw" non-limitingly refers to a screw comprising a screw head, optionally a shaft, at least one threaded portion and a tip. The screw head takes up the torque exerted by a tightening tool, for example, a screwdriver or a wrench, and applies a pressing force.

The shaft can be a smooth cylindrical or conical part.

The threaded portion ensures the tensioning of the connection by screwing by way of a helical projection also referred to as the thread, which is intended to be inserted while rotating in the substrate.

The tip ensures the guiding of the screw, or even the drilling of the substrate, for example, in wood, metal or in a threaded nut, in which the screw is tightened.

The screw sockets are varied and each have their own particularities, and therefore allow different uses. The socket has an impact on the tightening torque, the wear and the tightening efficiency. There are several kinds, some of which are very common, and others a little rarer and less used. These include:
- the slotted or flat head screw, which has a slot on the screw head, allowing it to be fixed using a flat screwdriver,
- the crosshead screw, also called the Phillips head screw, which has a small cross on the screw head. It is used in conjunction with a Phillips screwdriver. It is also recognizable by the marking "PH" (for Phillips),
- the Pozidriv screw, which resembles the Phillips screw due to the presence of a small cross. The Pozidriv screw also has an x marking that differentiates it from the Phillips screw,
- the six-lobed screw socket, also called the Torx screw, which is recognizable by its star shape,
- the socket head cap screw, also known as the Allen screw, and
- the square screw socket, also called the Robertson screw.

Fastening screws are usually made from steel. When high resistance to weather or corrosion is required, such as for small fastening screws or medical implants, materials such as stainless steel or titanium and titanium alloys may be employed.

From EP 0172130, a screw is known that can be driven by different sizes of Torx-type screwdrivers. This screw allows greater flexibility in the use of tools for screwing these screws, in the particular field of orthopedic surgery, these screws being intended to be inserted into a bone to allow consolidation thereof.

However, this document does not disclose the possibility for the screw head to be driven by various shapes of screwdriver heads, i.e., sockets.

Document WO2003025403 discloses a screw comprising a recess having three non-circular superimposed stages, the first stage having a hollow hexagonal socket of a first diameter, the second stage having a hollow hexagonal socket of a second diameter smaller than the first diameter, which is rotated angularly by an angle of 30° relative to the first socket along an axis perpendicular to the main plane of the socket, and a third stage with a pentagonal socket with a third diameter smaller than the second diameter.

In the present description, the diameter of a stage extending perpendicularly to an axis relates to the largest dimension of the recess in a plane perpendicular to the axis. In the case of a recess formed by a cylinder with a hexagonal base, the diameter of the recess is twice the radius of the inscribed circle. Many types of screw head sockets can be used in bone surgery. Medical regulations require that all the risks inherent in the use of implantable materials be analyzed and that all possible actions be taken to minimize the impact in terms of performance and safety for the patient. From this perspective, the need to allow material extraction—whatever the reasons or circumstances—is a requirement. There is therefore a need to be able to ensure that the majority of the standard screwdrivers used in surgery will be able to cooperate with the most commonly used sockets in order to extract them from the patient's body.

No document of the prior art provides for the possibility that the screw can be removed by two screwdrivers having substantially identical dimensions when the first and the second screwdriver have different types of sockets.

There is therefore a need to further improve the flexibility of use of various tools making it possible to tighten these screws, but above all to unscrew them and to be able to meet the aforementioned regulatory obligation.

BRIEF SUMMARY

One aim of the present disclosure is particularly to remedy all or part of the aforementioned drawbacks.

To this end, there is provided a bone anchoring screw comprising a head, a shaft, for example, cylindrical, and a threaded portion arranged successively along a common axis, the head having a recess comprising at least two stages arranged in succession along the common axis, the first stage having a diameter larger than the diameter of the second stage. According to the present disclosure, one of the two stages comprises at least one socket of a first type and the other of the two stages comprises at least one socket of the first type and one other type.

For example, the socket of the first type and the other socket can respectively have six lobes (according to the ISO 10664 standard) or a hexagon socket (according to the ISO 4762 or ISO 10642 standard).

According to one possibility, a stage can extend at least between a transverse surface (possibly a crown) arranged on the side of the shaft forming a shoulder (facing the head on which a screwdriver can rest) and a transverse crown arranged on the side of the head (that is to say, axially on the side opposite the shaft), the stage having a recess formed by the union (in the geometrical sense) of a six-lobed socket and a hexagon socket head cap, each of the sockets being centered on the common axis and opening on the side of the head. Also, the median transverse planes of each of the sockets can be combined.

Advantageously, the stage may have, in a section transverse to the common axis, a contour successively having, in alternation, a vertex of the hexagon socket head cap and a vertex of a six-lobed socket.

A stage may be a cylinder, the base of which has the contour resulting from a six-lobed contour and a six-sided contour and terminating in a transverse shoulder.

According to a particular embodiment, the angle formed between two successive vertices is substantially equal to 30° around the common axis.

More precisely, the six-lobed socket may have a radius $r_{6lc}$ of a circumscribed circle and a radius $r_{6li}$ of an inscribed circle and the hexagon socket head cap may have a radius $r_{6pc}$ of a circumscribed circle and a radius $r_{6pi}$ of an inscribed circle, and the radii satisfy the following inequality:

$$r_{6li} < r_{6pi} = \frac{\sqrt{3}}{2} r_{6pc} < r_{6lc}. \quad \text{[Math. 1]}$$

The recess of the stage may further comprise the union (in the geometric sense) of a Z-type crosshead socket and an H-type crosshead socket.

The four small branches of the Z-type crosshead socket may be contained in the four branches of the H-type crosshead socket ("contained in" means to fit into the recess formed by). Preferably, the diameter of the H-type socket may be larger than the diameter of the hexagon socket head cap. A vertex of a large branch of a Z-type socket, the center of the socket, and a vertex of a hexagon socket head cap may be aligned.

According to one possibility, the two stages may be identical or the stage comprising at least the socket of the first type can conform to the other stage described above.

The screw may further comprise an intermediate stage arranged between the first and the second stage. The recess of the intermediate stage may comprise fewer types of sockets than the recess of the first and/or second stage.

Z and/or H and/or square and/or slot type sockets can be obtained by homothety between two stages. The six-sided and/or six-lobed type sockets can be obtained by homothety and rotation between two stages.

BRIEF DESCRIPTION OF THE DRAWINGS

Other advantages and particularities of the present disclosure will become apparent on reading the detailed description of implementations and embodiments, which are in no way limiting, with regard to the accompanying drawings, in which.

DETAILED DESCRIPTION

Figure 1:
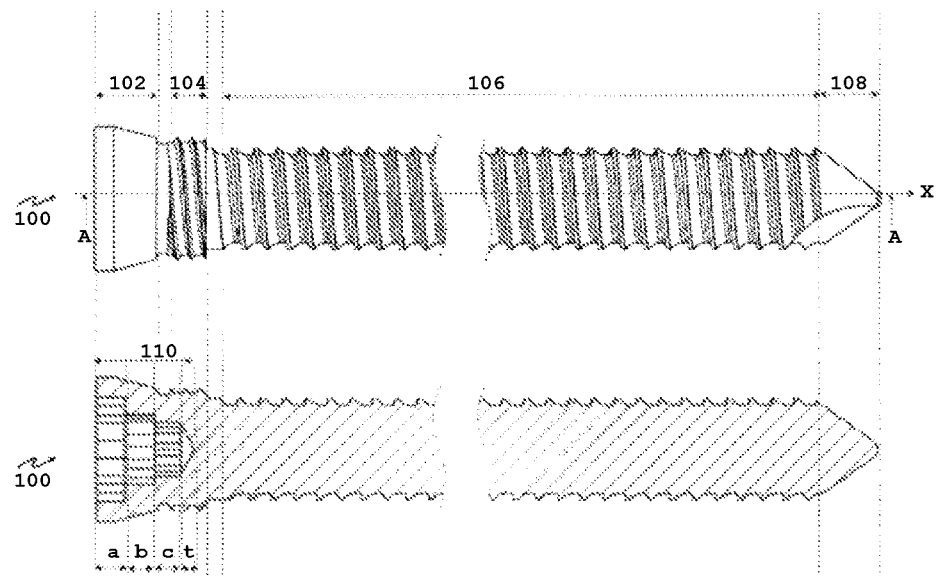
FIG. 1 illustrates, in its upper part, a perspective view with cutaway of an embodiment of a screw according to a first embodiment; the lower part is a longitudinal section of the screw along lines AA of the upper part.

Since the embodiments described hereinafter are not limiting in nature, it is possible, in particular, to consider variants of embodiments of the present disclosure that comprise only a selection of the features that are described, provided that this selection of features is sufficient to confer a technical advantage or to differentiate embodiments of the present disclosure from the prior art. This selection comprises at least one preferably functional feature without structural details, or with only a portion of the structural details if this portion alone is sufficient to confer a technical advantage or to differentiate the present disclosure from the prior art.

Although the present disclosure is not limited to screws for orthopedic use, it finds particular utility in this field.

A first embodiment of a screw 100 according to the present disclosure is described with reference to the upper part of FIG. 1. The screw 100 has a longitudinal axis X and comprises successively, in a direction of the longitudinal axis X, a head 102, a first threaded portion 104, a second threaded portion 106 and a tip 108.

A first transition portion (not numbered), also called the first shaft portion, is disposed axially between the head 102 and the first threaded portion 104.

A second transition portion (not numbered), also called the second shaft portion, is disposed axially between the first threaded portion 104 and the second threaded portion 106.

With reference to the lower part of FIG. 1, it is observed that the screw comprises, on the side of its head 102, a recess 110 comprising three stages arranged successively in the aforementioned direction of the longitudinal axis X, respectively referenced a, b, c in FIG. 1, but are 102a, 102b and 102c in the present description. The recess 110 further comprises an end countersink, referenced t in the figure, but 102t in the present description.

In this example, the axial extension of the recess 110 is 4.37 mm and the half-cone angle formed by countersinking is 62°.

The depth of the recess 110 may advantageously be greater than the depth of the head 102, preferably greater than the depth of the head 102 and of the first transition portion, more preferably greater than the depth of the head 102 and of the first transition portion and a fraction of the depth of the first threaded portion 104. This characteristic makes it possible to optimize the compactness of the screw.

Each of the stages has a diameter smaller than the stage immediately adjacent to the side of the head 102 and larger than the diameter of the stage immediately adjacent to the side of the tip 108.

The first stage 102a has a diameter smaller than the outside diameter of the screw 100.

The cone 102t has a diameter smaller than the diameter of the last stage.

The series of diameters, respectively da, db, dc of the stages 102a, 102b, 102c is a decreasing series.

Figure 2:
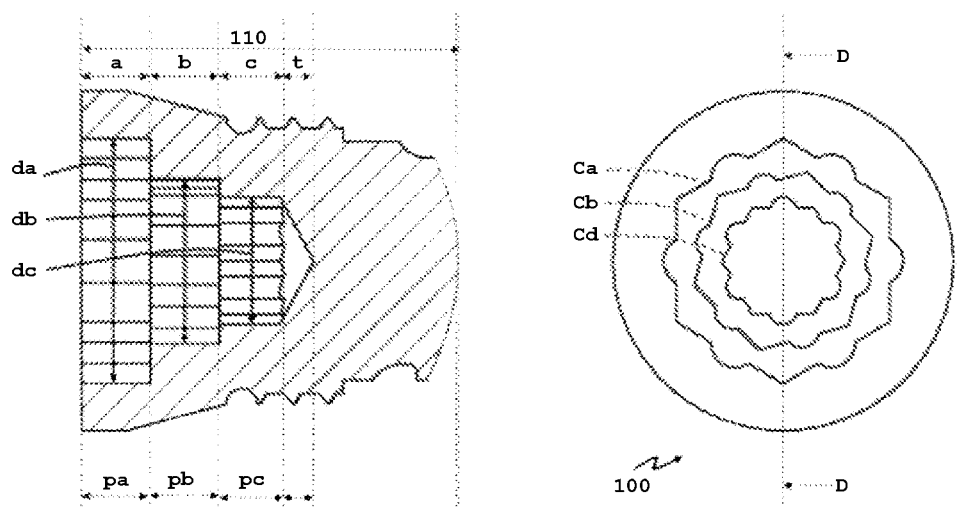
FIG. 2 shows, in the left part, a section along lines DD of the right part; the right part shows a drawing of the upper part of FIG. 1.

With reference to the left part of FIG. 2, it should be noted that the series of depths, respectively pa, pb, pc of the stages 102a, 102b, 102c can be a decreasing sequence.

Alternatively, the series of depths of the stages can be constant, increasing or arbitrary.

The contours, respectively, Ca, Cb and Cd, of the stages with 102a, 102b and 102c are shown.

Each of the contours results from the union of two surfaces, one of the surfaces resulting from a six-lobed socket according to the ISO 10664 standard and the other from the surfaces resulting from a hexagon socket head cap.

Figure 3:
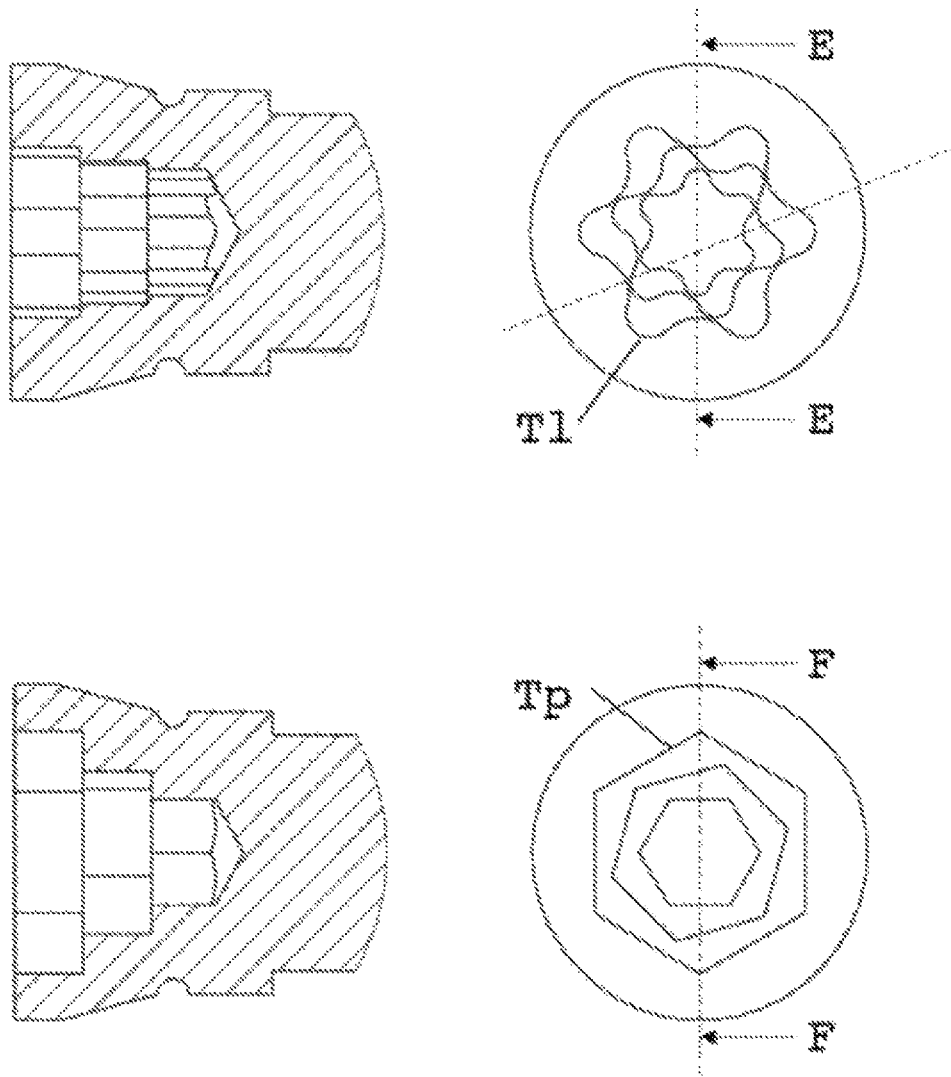
FIG. 3 comprises an upper part showing, in the left part, a section along lines EE of the right part, the right part showing a drawing of a three-stage screw, each of the stages comprising a six-lobed socket according to the ISO 10664 standard; the lower part has, in the left part, a section along lines FF of the right part, the right part showing a drawing of a three-stage screw, each of the stages comprising a hexagon socket head cap.

For a good understanding of the present disclosure, FIG. 3 shows two screws.

With reference to the upper part of FIG. 3:
the dimensions of the first, second, and third stages conform, respectively, to the dimensions T25, T15 and T8 of the ISO 10664 standard, that is to say, the respective internal diameters of 3.25 mm, 2.40 mm and 1.75 mm (inscribed circles with respective radius 1.652 mm, 1.20 mm and 0.875 mm),
the second stage is angularly rotated by 45° relative to the first stage,
the third stage is angularly rotated by 45° relative to the second stage.

With reference to the lower part of FIG. 3:
the dimensions of the first, second and third stages conform, respectively, to the dimensions M5, M4, M2.5 of the ISO 4762 standard, that is to say, the distance between two respective opposite faces is 4 mm, 3 mm and 2 mm (inscribed circles with respective radius 2 mm, 1.5 mm and 1 mm and circumscribed circles with radius),
the second stage is angularly rotated by 45° relative to the first stage,
the third stage is angularly rotated by 45° relative to the second stage.

Also, in the example shown in FIG. 2:
each of the stages has a depth of 1.30 mm,
each of the stages is rotated angularly by 45° about the common axis with respect to the previous/next stage,
the countersink has a dimension of 2.47 mm.

The recess 110 is the result of the union of the two three-stage screws that have just been described.

Each of the contours successively has, alternately, a vertex of a hexagon socket head cap and a vertex of a six-lobed socket. The angle formed between two consecutive vertices is 30°, so as to obtain a contour invariance by 60° rotation.

For each of the stages, the median transverse planes of the six-lobed socket and the hexagon socket head cap are the same.

When a six-lobed socket is rotated centered on a hexagon socket head cap and rotated angularly so that the resulting contour alternately has a vertex of a hexagon socket head cap and a vertex of a six-lobed socket, it is necessary that:

the radius r6lc of the circumscribed circle of the six-lobed socket is greater than the radius r6pi of the inscribed circle (also referred to as the apothem) of the hexagon socket head caps: r6lc>r6pi,
the radius r6pc of the circumscribed circle of the hexagon socket head caps is greater than the radius r6li of the inscribed circle of the six-lobed sockets, r6pc>r6li,
the radius r6pi of the inscribed circle of the hexagon socket head caps is greater than the radius r6li of the inscribed circle of the six-lobed sockets: r6pi>r6li.

These conditions can be summarized by the following inequality:

$$r_{6li} < r_{6pi} = \frac{\sqrt{3}}{2} r_{6pc} < r_{6lc} \quad \text{[Math. 1]}$$

These conditions are verified for each of the three stages, as shown in the following table:

TABLE 1

|  |  | $r_{6li}$ | $r_{6pi}$ | $r_{6pc}$ | $r_{6lc}$ |
|---|---|---|---|---|---|
| Stage 1 | T25 and M5 | 1625 | 2000 | 2309 | 2250 |
| Stage 2 | T15 and M4 | 1200 | 1500 | 1732 | 1675 |
| Stage 3 | T8 and M2.5 | 0.875 | 1000 | 1155 | 1200 |

The geometric transformation that transforms the first contour Ca into the second contour Cb is a 45° angle similarity. The geometric transformation that transforms the second contour Cb into the third contour Cd is also a 45° angle similarity.

Such a screw can be formed by machining or by additive manufacturing.

The material used to form the screw can be a material having antibacterial properties.

According to a first variant of the present disclosure, not shown and described only for how it differs from the first embodiment, the screw may have only two stages instead of three.

According to a second variant of the present disclosure, not shown and described only for how it differs from the first variant, one of the stages has a contour formed by two different types of sockets of substantially identical diameter, the other of the stages comprising a single socket, of the same type as one of the types forming the contour.

Figure 4:
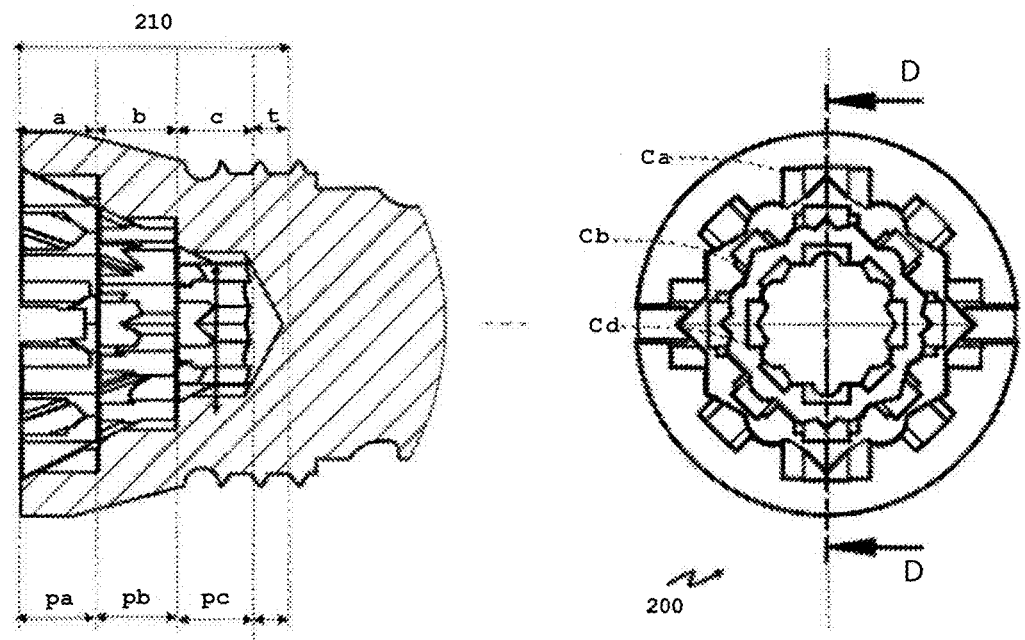
FIG. 4 shows, in the left part, a section along lines DD of the right part; the right part shows a drawing of a screw according to a second embodiment.

Referring to FIG. 4, a screw 200 is shown according to a second embodiment according to the present disclosure.

The screw 200 comprises a recess 210 also formed by three stages a, b, c, referenced 210a, 210b, 210c in the description.

Figure 5:
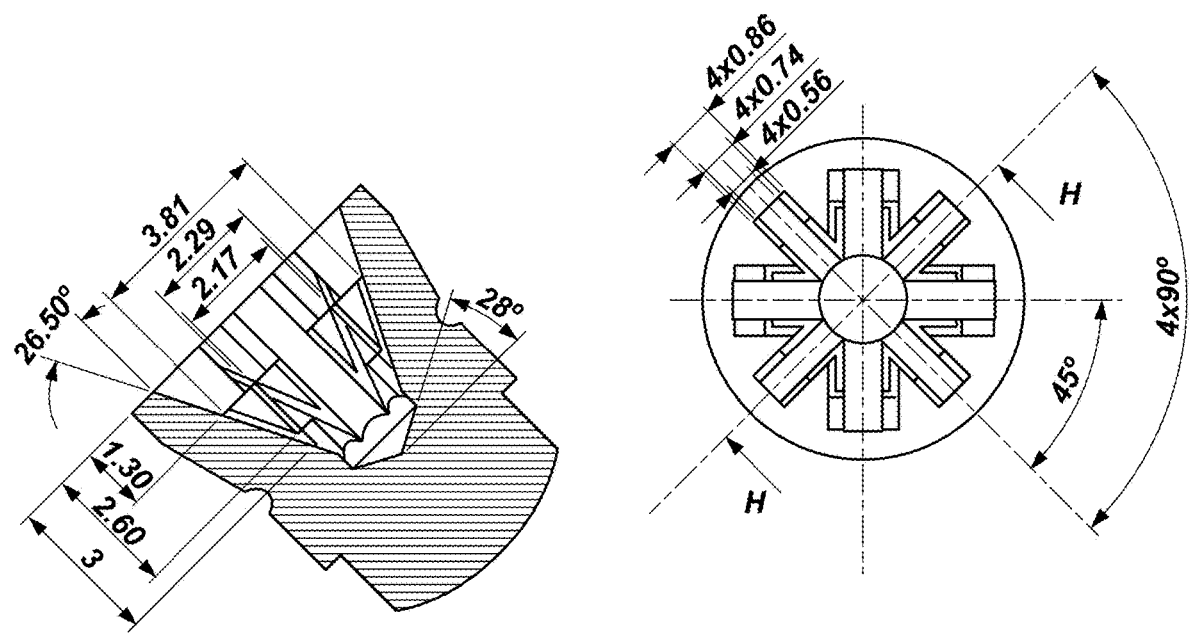
FIG. 5 shows, in the left part, a section along lines HH of the right part, the right part showing a drawing of a three-stage screw, each of the stages comprising an H-type crosshead socket according to the ISO 4757 standard.
Figure 6:
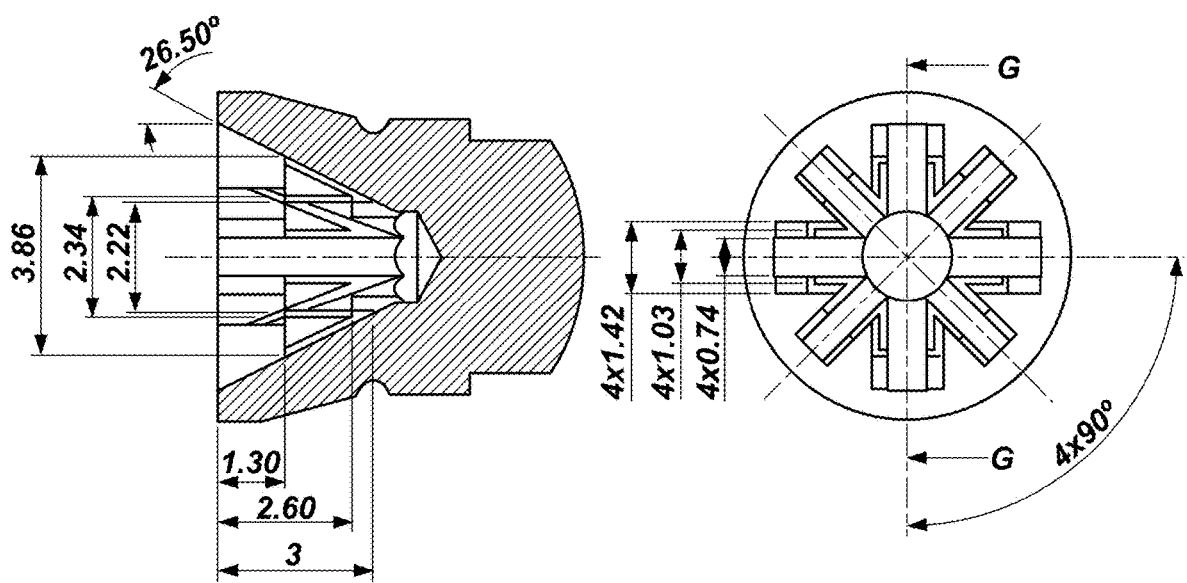
FIG. 6 shows, in the left part, a section along lines GG of the right part, the right part showing a drawing of a three-stage screw, each of the stages comprising a Z-type crosshead socket according to the ISO 4757 standard.

As will be better understood in the light of the description of FIGS. 5 and 6, each of the stages is formed by:
a six-lobed socket according to the ISO 10664 standard,
a hexagon socket head cap,
a Z-type crosshead socket (Pozidriv type),
an H-type crosshead socket (Phillips type).

An H-type crosshead socket has four branches forming a cross, each of the branches having the same dimensions.

A Z-type crosshead socket is in the shape of an 8-pointed star: four large branches like those of the H-type sockets, and four small branches of the same dimensions and forming a cross rotated by 45° with respect to the cross formed by the four large branches. The dimension of each of the four small branches is smaller than that of the large branches.

As can be seen in FIG. 5, the various H-type crosshead sockets of each of the stages are centered on one another and are not turned with respect to one another along the common axis between two successive stages.

Still with reference to FIG. 5:
the first stage comprises an H-type crosshead socket of size PH3 in accordance with the ISO 4757 standard, each of the branches having the same dimension, the diameter of the socket being 3.81 mm,
the second stage comprises an H-type crosshead socket of size PH2 in accordance with the ISO 4757 standard, each of the branches having the same dimension, the diameter of the socket being 2.29 mm,
the third stage comprises an H-type crosshead socket of size PH1 in accordance with the ISO 4757 standard, each of the branches having the same dimension, the diameter of the socket being 2.22 mm.

With reference to FIG. 6:
the first stage comprises a Z-type crosshead socket of size PZ3 in accordance with the ISO 4757 standard, the large branches having a diameter of 3.86 mm, the small branches having a diameter of 3.81 mm,
the second stage comprises a Z-type crosshead socket of size PZ2 in accordance with the ISO 4757 standard, the large branches having a diameter of 2.34 mm, the small branches having a diameter of 2.29 mm,
the third stage comprises a Z-type crosshead socket of size PZ1 in accordance with the ISO 4757 standard, the large branches having a diameter of 2.22 mm, the small branches having a diameter of 2.17 mm.

As can be seen in FIG. 6, on each stage, the four branches of the H-type crosshead socket are rotated by 45° about the common axis with respect to the four large branches of the Z-type crosshead socket.

Cleverly, the small diameter branches of a Z-type socket of one stage have an extension that is compatible with (and therefore greater than) that of an H-type crosshead socket for the same stage.

With reference to FIG. 4, and more particularly to the figure on the left, it is noted that for each of the three stages, the median transverse plane of the Z-type crosshead socket coincides with each of the median transverse planes of the six-lobed socket and of the hexagon socket head cap.

According to a first variant of the second embodiment, not shown and described only for how it differs from the first embodiment, the screw may have only two stages instead of three.

According to a second variant of the second embodiment, not shown and described only for how it differs from the second embodiment, and possibly combinable with the first variant of the second embodiment, or the first embodiment or one or several of its variants, one of the stages comprises only (or even only one of) the two H-type and/or Z-type crosshead sockets.

According to a third variant of the second embodiment, not shown and described only for how it differs from the first and/or the second embodiment, and possibly combinable with the first variant, or the first embodiment or one of its variants, one of the stages comprises only (or even only one of) two six-lobed sockets and/or hexagon socket head caps.

Figure 7:
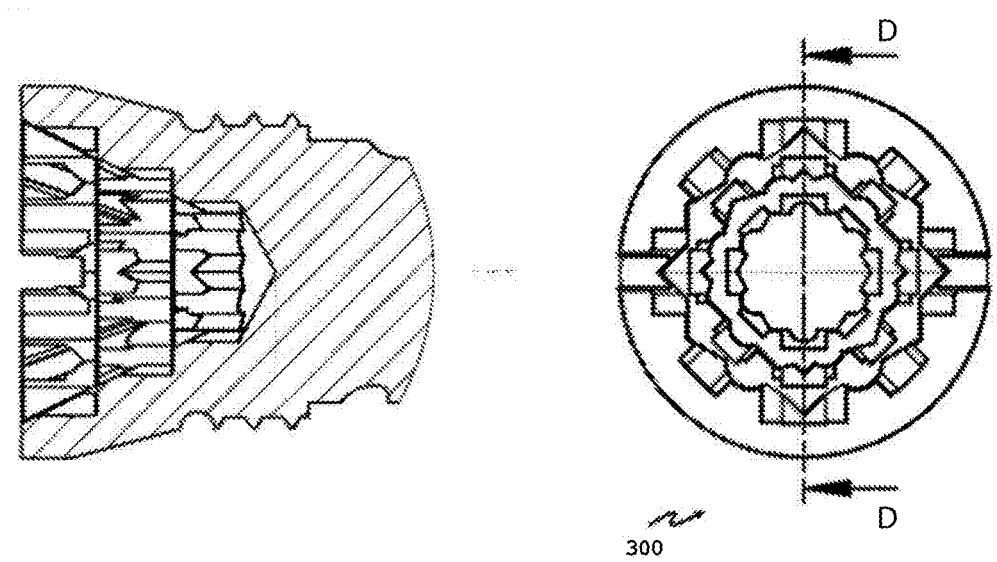
FIG. 7 shows, in the left part, a section along lines DD of the right part; the right part shows a drawing of a screw according to a third embodiment.

Referring to FIG. 7, a screw 300 is shown according to a third embodiment according to the present disclosure.

Each of the stages is formed by:
a six-lobed socket according to the ISO 10664 standard,
a hexagon socket head cap,
a Z-type crosshead socket (Pozidriv type),
an H-type crosshead socket (Phillips type).

Figure 8:
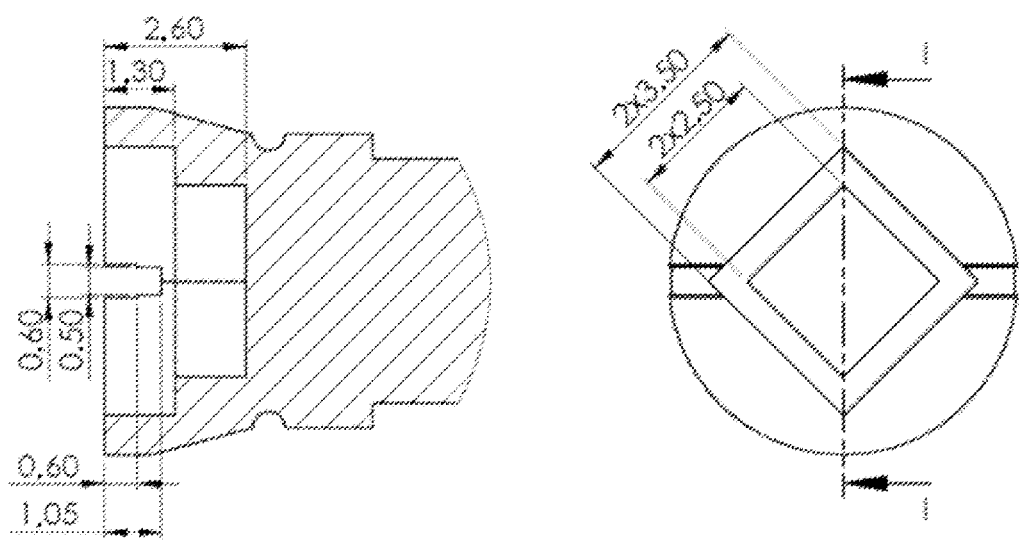
FIG. 8 shows, in the left part, a section along lines II of the right part, the right part showing a drawing of a three-stage screw, the first and the second stage comprising a square screw.

As will be better understood in the light of the description of FIG. 8:
the first and second stages each have a square socket,
the first stage has two slot sockets.

As can be seen in FIG. 8, the various square sockets of the stages are centered on one another and are not turned with respect to one another along the common axis between two successive stages.

Still with reference to FIG. 8:
the first stage comprises a square socket of side 3.50, having a diameter of 4.95 mm,
the second stage comprises a square socket of side 2.50, having a diameter of 3.54 mm.

The first stage further comprises two slot sockets. Each of the slot sockets has an extension plane that is transverse to the common axis. The two extension planes are combined, and perpendicular to the axial plane passing through two opposite vertices of one of the squares.

With reference to FIG. 7, and more particularly to the figure on the left, it is noted that for each of the first two stages, the median transverse plane of the square socket coincides with each of the median transverse planes of the six-lobed socket and of the hexagon socket head cap.

The present disclosure is naturally not limited to the examples that have just been described and numerous modifications can be made to these examples without departing from the scope of the present disclosure. In addition, the various features, forms, variants, and embodiments of the present disclosure can be grouped together in various combinations as long as they are not incompatible or mutually exclusive.

The invention claimed is:

1. A bone anchoring screw, comprising:
a head;
a shaft; and
a threaded portion;
wherein the head, the shaft, and the threaded portion are arranged successively along a common axis, the head has a recess comprising at least a first stage, a second stage, and an intermediate stage between the first stage and the second stage, the first stage, intermediate stage, and second stage arranged in succession along the common axis, the first stage having a diameter larger than a diameter of the second stage, and one stage of the first and second stages comprises at least one socket of a first type and another stage of the first and second stages comprises at least one socket of the first type and at least one socket of another type, further comprising an intermediate stage between the first stage and the second stage.

2. The bone anchoring screw of claim 1, wherein the recess in the intermediate stage comprises fewer types of sockets than the recess in the first stage and/or the second stage.

3. A bone anchoring screw, comprising:
a head;
a shaft; and
a threaded portion;
wherein the head, the shaft, and the threaded portion are arranged successively along a common axis, the head has a recess comprising at least two stages arranged in succession along the common axis, a first stage of the at least two stages has a diameter larger than a diameter of a second stage of the at least two stages, and one stage of the at least two stages comprises at least one socket of a first type and another stage of the at least two stages comprises at least one socket of the first type and at least one socket of another type, and wherein at least one of the sockets of one stage of the at least two stages can be obtained by homothety of at least one of the sockets of another stage of the at least two stages or obtained by homothety and rotation of at least one of the sockets of the another stage.

4. A bone anchoring screw, comprising:
a head;
a shaft; and
a threaded portion;
wherein the head, the shaft, and the threaded portion are arranged successively along a common axis, the head has a recess comprising at least two stages arranged in succession along the common axis, a first stage of the at least two stages has a diameter larger than a diameter of a second stage of the at least two stages, and one stage of the at least two stages comprises at least one socket of a first type and another stage of the at least two stages comprises at least one socket of the first type and at least one socket of another type, and wherein, in the another stage, the at least one socket of the first type and the at least one socket of the another type are, respectively, a six-lobed socket and a hexagon socket head cap, or the at least one socket of the first type and the at least one socket of the another type are, respectively, a hexagon socket head cap and a six-lobed socket.

5. The bone anchoring screw of claim 4, wherein at least one stage of the at least two stages extends at least between a transverse surface on a side of the shaft forming a shoulder and a transverse crown on a side of the head, the at least one stage of the at least two stages having a recess formed by a union of a six-lobed socket and a hexagon socket head cap, each of the six-lobed socket and the hexagon socket being centered on the common axis and opening on the side of the head.

6. The bone anchoring screw of claim 5, wherein the at least one stage has, in a section transverse to the common axis, a contour successively having, in alternation, a vertex of the hexagon socket head cap and a vertex of a six-lobed socket.

7. The bone anchoring screw of claim 6, wherein an angle formed between two successive vertices is substantially equal to 30° around the common axis.

8. The bone anchoring screw of claim 6, wherein the six-lobed socket has a radius role of a circumscribed circle and the hexagon socket head cap has a radius $r_{6pc}$ of a circumscribed circle and a radius $r_{6pi}$ of an inscribed circle, and the radii satisfy the following inequality:

$$r_{6pi} = \frac{\sqrt{3}}{2} r_{6pc} < r_{6lc}.$$

9. The bone anchoring screw of claim 5, wherein at least one stage of the at least two stages of the recess comprises a union of a Z-type crosshead socket and an H-type crosshead socket.

10. The bone anchoring screw of claim 9, wherein four small branches of the Z-type crosshead socket are contained in four branches of the H-type crosshead socket.

11. The bone anchoring screw of claim 9, wherein a diameter of the H-type crosshead socket is larger than a diameter of the hexagon socket head cap.

12. The bone anchoring screw of claim 9, wherein a vertex of a large branch of the Z-type crosshead socket, a center of the socket, and a vertex of the hexagon socket head cap are aligned.

13. The bone anchoring screw of claim 4, wherein the types of sockets of the at least two stages are the same.

14. The bone anchoring screw of claim 7, wherein the six-lobed socket has a radius role of a circumscribed circle and the hexagon socket head cap has a radius $r_{6pc}$ of a circumscribed circle and a radius $r_{6pi}$ of an inscribed circle, and the radii satisfy the following inequality:

$$r_{6pi} = \frac{\sqrt{3}}{2} r_{6pc} < r_{6lc}.$$

15. The bone anchoring screw of claim 8, wherein at least one stage of the at least two stages of the recess comprises a union of a Z-type crosshead socket and an H-type crosshead socket.

16. The bone anchoring screw of claim 15, wherein four small branches of the Z-type crosshead socket are contained in four branches of the H-type crosshead socket.

17. The bone anchoring screw of claim 10, wherein a diameter of the H-type crosshead socket is larger than a diameter of the hexagon socket head cap.

18. The bone anchoring screw of claim 11, wherein a vertex of a large branch of the Z-type crosshead socket, a center of the socket, and a vertex of the hexagon socket head cap are aligned.

* * * * *